(12) United States Patent
Eisinger

(10) Patent No.: US 11,553,913 B2
(45) Date of Patent: Jan. 17, 2023

(54) ELECTRICALLY-DETERMINING TISSUE CUT WITH SURGICAL STAPLING APPARATUS

(71) Applicant: Covidien LP, Mansfield, MA (US)

(72) Inventor: Joseph Eisinger, Northford, CT (US)

(73) Assignee: COVIDIEN LP, Mansfield, MA (US)

( * ) Notice: Subject to any disclaimer, the term of this patent is extended or adjusted under 35 U.S.C. 154(b) by 14 days.

(21) Appl. No.: 17/148,722

(22) Filed: Jan. 14, 2021

(65) Prior Publication Data
US 2021/0244408 A1 Aug. 12, 2021

Related U.S. Application Data

(63) Continuation of application No. 62/972,781, filed on Feb. 11, 2020.

(51) Int. Cl.
*A61B 17/068* (2006.01)
*A61B 17/072* (2006.01)
*A61B 17/00* (2006.01)

(52) U.S. Cl.
CPC ........ *A61B 17/0686* (2013.01); *A61B 17/072* (2013.01); *A61B 2017/00022* (2013.01);
(Continued)

(58) Field of Classification Search
CPC . A61B 17/068; A61B 17/0686; A61B 17/072; A61B 17/115; A61B 17/1155; A61B 2017/07285; A61B 2017/00022; A61B 2017/00026; A61B 2017/0003; A61B 2017/00115; A61B 2017/00128; A61B 2017/00398; A61B 2017/00477; A61B 2017/00734; A61B 34/30; A61B 34/32; G01D 5/14
(Continued)

(56) References Cited

U.S. PATENT DOCUMENTS

| | | |
|---|---|---|
| 37,165 A | 12/1862 | Gary |
| 3,209,754 A | 10/1965 | Brown |

(Continued)

FOREIGN PATENT DOCUMENTS

| | | |
|---|---|---|
| CN | 101683284 A | 3/2010 |
| CN | 102648864 A | 8/2012 |

(Continued)

OTHER PUBLICATIONS

Detemple, P., "Microtechnology in Modem Health Care", Med Device Technol. 9(9):18-25 (1998).
(Continued)

*Primary Examiner* — Stephen F. Gerrity
*Assistant Examiner* — Linda J Hodge
(74) *Attorney, Agent, or Firm* — Carter, DeLuca & Farrell LLP

(57) ABSTRACT

A surgical stapling apparatus includes an end effector and an electronics assembly, the end effector having an anvil assembly and a cartridge assembly. The anvil and cartridge assemblies are positionable between an open position and a closed position to selectively grasp tissue therebetween. The electronics assembly is supported in the end effector and configured to determine a condition of the grasped tissue based on an amount of current in an electrical circuit defined by the anvil and cartridge assemblies.

20 Claims, 6 Drawing Sheets

(52) U.S. Cl.
CPC .............. *A61B 2017/07257* (2013.01); *A61B 2017/07271* (2013.01); *A61B 2017/07285* (2013.01)

(58) Field of Classification Search
USPC .......................................... 227/175.1, 180.1
See application file for complete search history.

(56) References Cited

U.S. PATENT DOCUMENTS

| | | |
|---|---|---|
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A * | 6/1996 | Boiarski ................ A61B 90/98 600/101 |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |

(56) References Cited

U.S. PATENT DOCUMENTS

| | | |
|---|---|---|
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |

(56) References Cited

U.S. PATENT DOCUMENTS

| | | |
|---|---|---|
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,837,080 B2 * | 11/2010 | Schwemberger .... A61B 17/115 227/176.1 |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 3,006,885 A1 | 8/2011 | Marczyk |
| 3,006,887 A1 | 8/2011 | Marczyk |
| 3,011,551 A1 | 9/2011 | Marczyk et al. |
| 3,020,742 A1 | 9/2011 | Marczyk |
| 3,025,199 A1 | 9/2011 | Whitman et al. |
| 3,038,044 A1 | 10/2011 | Viola |
| 3,052,024 A1 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| 8,685,004 B2 | 4/2014 | Zemlock et al. |
| 9,192,381 B2 | 11/2015 | Marczyk |
| 9,364,222 B2 | 6/2016 | Zemlok et al. |
| 9,370,360 B2 | 6/2016 | Marczyk |
| 9,370,361 B2 | 6/2016 | Viola et al. |
| 9,433,415 B2 | 9/2016 | Marczyk et al. |
| 9,480,492 B2 | 11/2016 | Aranyi et al. |
| 9,585,659 B2 | 3/2017 | Viola et al. |
| 10,135,242 B2 * | 11/2018 | Baber .................... A61B 90/92 |
| 10,492,814 B2 | 12/2019 | Snow et al. |
| 10,722,222 B2 | 7/2020 | Aranyi |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0006429 A1 | 1/2005 | Wales et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0135600 A1 | 6/2008 | Hiranuma et al. |

(56) References Cited

U.S. PATENT DOCUMENTS

| | | |
|---|---|---|
| 2008/0169329 A1 | 7/2008 | Shelton et al. |
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2009/0018624 A1 | 1/2009 | Levinson et al. |
| 2009/0090201 A1 | 4/2009 | Viola |
| 2009/0090763 A1 | 4/2009 | Zemlok et al. |
| 2010/0200636 A1 | 8/2010 | Zemlok et al. |
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0062211 A1 | 3/2011 | Ross et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0175400 A1 | 7/2012 | Viola et al. |
| 2012/0193393 A1 | 8/2012 | Viola et al. |
| 2012/0198288 A1 | 8/2012 | Njo et al. |
| 2012/0211542 A1* | 8/2012 | Racenet ............ A61B 17/07207 227/175.1 |
| 2012/0220989 A1 | 8/2012 | Zemlok et al. |
| 2012/0223121 A1 | 9/2012 | Viola et al. |
| 2012/0241494 A1 | 9/2012 | Marczyk |
| 2012/0277790 A1 | 11/2012 | Zemlok et al. |
| 2012/0298718 A1 | 11/2012 | Marczyk |
| 2012/0298720 A1 | 11/2012 | Marczyk |
| 2016/0265938 A1* | 9/2016 | Hryb .................... A61B 17/072 |
| 2018/0250002 A1* | 9/2018 | Eschbach ........... A61B 17/0682 |
| 2018/0353186 A1* | 12/2018 | Mozdzierz ........... A61B 17/072 |
| 2019/0059884 A1 | 2/2019 | Shelton, IV et al. |
| 2019/0201034 A1 | 7/2019 | Shelton, IV et al. |

FOREIGN PATENT DOCUMENTS

| | | |
|---|---|---|
| CN | 107687985 A | 2/2018 |
| EP | 0537570 A2 | 4/1993 |
| EP | 0647431 A2 | 4/1995 |
| EP | 0738501 A1 | 10/1996 |
| EP | 0770354 A1 | 5/1997 |
| EP | 1070487 A2 | 1/2001 |
| EP | 1201196 A1 | 5/2002 |
| EP | 1658817 A1 | 5/2006 |
| EP | 1813203 A2 | 8/2007 |
| FR | 2 849 589 A1 | 7/2004 |
| WO | 9414129 A1 | 6/1994 |
| WO | 9729694 A1 | 8/1997 |
| WO | 9740760 A1 | 11/1997 |
| WO | 9837825 A1 | 9/1998 |
| WO | 1999/52489 A1 | 10/1999 |
| WO | 0234140 A2 | 5/2002 |
| WO | 03026511 A1 | 4/2003 |
| WO | 03030743 A2 | 4/2003 |
| WO | 2004032760 A2 | 4/2004 |
| WO | 2007030753 A2 | 3/2007 |
| WO | 2007/114868 A2 | 10/2007 |
| WO | 2007118179 A2 | 10/2007 |
| WO | 2007014355 A3 | 4/2009 |
| WO | 2009143092 A1 | 11/2009 |

OTHER PUBLICATIONS

Abridged Data Sheet, "DeepCover Secure Authenticator with 1-Wire SHA-256 and 512-Bit User EEPROM", Maxim Integrated Products, Inc. pp. 1-4; 42; Dec. 2012.

Data Sheet "DS28E15-1-Sire SHA-256 Secure Authenticator with 512-Bit User EEPROM"; IC-On-Line, Electronic Component Manufacturers, pp. 1-2; Aug. 2013.

* cited by examiner

ELECTRICALLY-DETERMINING TISSUE CUT WITH SURGICAL STAPLING APPARATUS

CROSS-REFERENCE TO RELATED APPLICATIONS

This application claims the benefit of and priority to U.S. Provisional Patent Application Ser. No. 62/972,781 filed Feb. 11, 2020, the entire disclosure of which is incorporated by reference herein.

TECHNICAL FIELD

This disclosure relates to surgical stapling apparatus and, more particularly, to structures and methods for determining tissue cut.

BACKGROUND

Fasteners have traditionally been used to replace suturing when joining various body structures such as, for example, the bowel or bronchus. Surgical stapling apparatus employed to apply these fasteners are generally designed to simultaneously cut and seal tissue to reduce the time and risks involved with anastomosis procedures.

Circular surgical stapling apparatus are employed by surgeons to apply one or more surgical fasteners, e.g., staples or two-part fasteners, to body tissue for the purpose of joining segments of body tissue together and/or for the creation of anastomoses. Circular surgical stapling apparatus generally include an annular fastener cartridge assembly that supports a plurality of annular rows of fasteners, an annular anvil assembly operatively associated with the fastener cartridge assembly which provides a surface against which the fasteners are formed upon a firing of the circular stapling apparatus, and an annular blade for cutting tissue.

SUMMARY

According to one aspect, a surgical stapling apparatus includes an end effector and an electronics assembly. The end effector has an anvil assembly and a cartridge assembly. The anvil and cartridge assemblies are positionable between an open position and a closed position to selectively grasp tissue therebetween. The electronics assembly is supported in the end effector and configured to determine a condition of the grasped tissue based on an amount of current in an electrical circuit defined by the anvil and cartridge assemblies.

In aspects, the surgical stapling apparatus may further include a knife supported in the cartridge assembly and positioned to contact the anvil assembly to change the amount of current in the electrical circuit. The electronics assembly may be configured to determine when the grasped tissue is cut by the knife based on the amount of current.

In various aspects, the current may be prevented from flowing through the electrical circuit before the tissue is grasped.

In certain aspects, the electronics assembly may include an inner coupler and an outer coupler that supports the inner coupler. The inner coupler may have a tubular body positioned to receive a center rod assembly of the anvil assembly therein. The outer coupler may include a coupling ring that depends therefrom and is positioned to receive the inner coupler therein. The coupling ring may be disposed in contact with a drive sleeve supported within the end effector.

The drive sleeve may be movable relative to the anvil assembly to enable the knife to cut through tissue grasped between the anvil assembly and the cartridge assembly.

In aspects, the electronic assembly may include a device communication bus system with a single data wire.

According to one aspect, a surgical stapling apparatus includes a powered surgical device and an adapter assembly extending distally from the powered surgical device and supporting an end effector. The end effector includes an anvil assembly and a cartridge assembly. The anvil and cartridge assemblies are positionable between an open position and a closed position to selectively grasp tissue therebetween. The end effector further includes a device communication bus system and a controller. The device communication bus system is supported in the cartridge assembly and electrically coupled to an electrical circuit defined by components of the end effector. The controller is electrically coupled to the device communication bus system and configured to determine a condition of the grasped tissue based on a condition of the electrical circuit determined by the device communication bus system.

In aspects, a first component of the components of the end effector may be positioned to contact the anvil assembly to change the condition of the electrical circuit. When the first component contacts the anvil assembly, the controller may be configured to output an indication that the grasped tissue is cut. The first component may include a knife. The drive sleeve may be movable relative to the anvil assembly to enable the knife to cut through tissue grasped between the anvil assembly and the cartridge assembly.

In various aspects, the condition of the electrical circuit may include an amount of current in the electrical circuit.

Is aspects, the surgical stapling apparatus may further include an inner coupler and an outer coupler disposed in the end effector. One or both of the inner coupler and the outer coupler may support the device communication bus system. The inner coupler may have a tubular body positioned to receive a center rod assembly of the anvil assembly therein. The outer coupler may include a coupling ring that depends therefrom and is positioned to receive the inner coupler therein. The coupling ring may be disposed in contact with a drive sleeve supported within the end effector.

In accordance with yet another aspect, a surgical stapling apparatus includes a powered surgical device, an adapter assembly, a device communication bus system, and a controller. The adapter assembly extends distally from the powered surgical device and supports an end effector configured to grasp tissue. The device communication bus system is supported in the end effector and is in contact with components of the end effector to define an electrical circuit. The controller includes a processor and a memory having instructions stored thereon, which when executed by the processor, cause the device communication bus system to measure a current in the electrical circuit to enable the processor to determine a condition of the grasped tissue.

Other aspects, features, and advantages will be apparent from the description, the drawings, and the claims that follow.

BRIEF DESCRIPTION OF DRAWINGS

The accompanying drawings, which are incorporated in and constitute a part of this specification, illustrate aspects of the disclosure and, together with a general description of the disclosure given above and the detailed description given below, serve to explain the principles of this disclosure, wherein.

DETAILED DESCRIPTION

Figure 1:
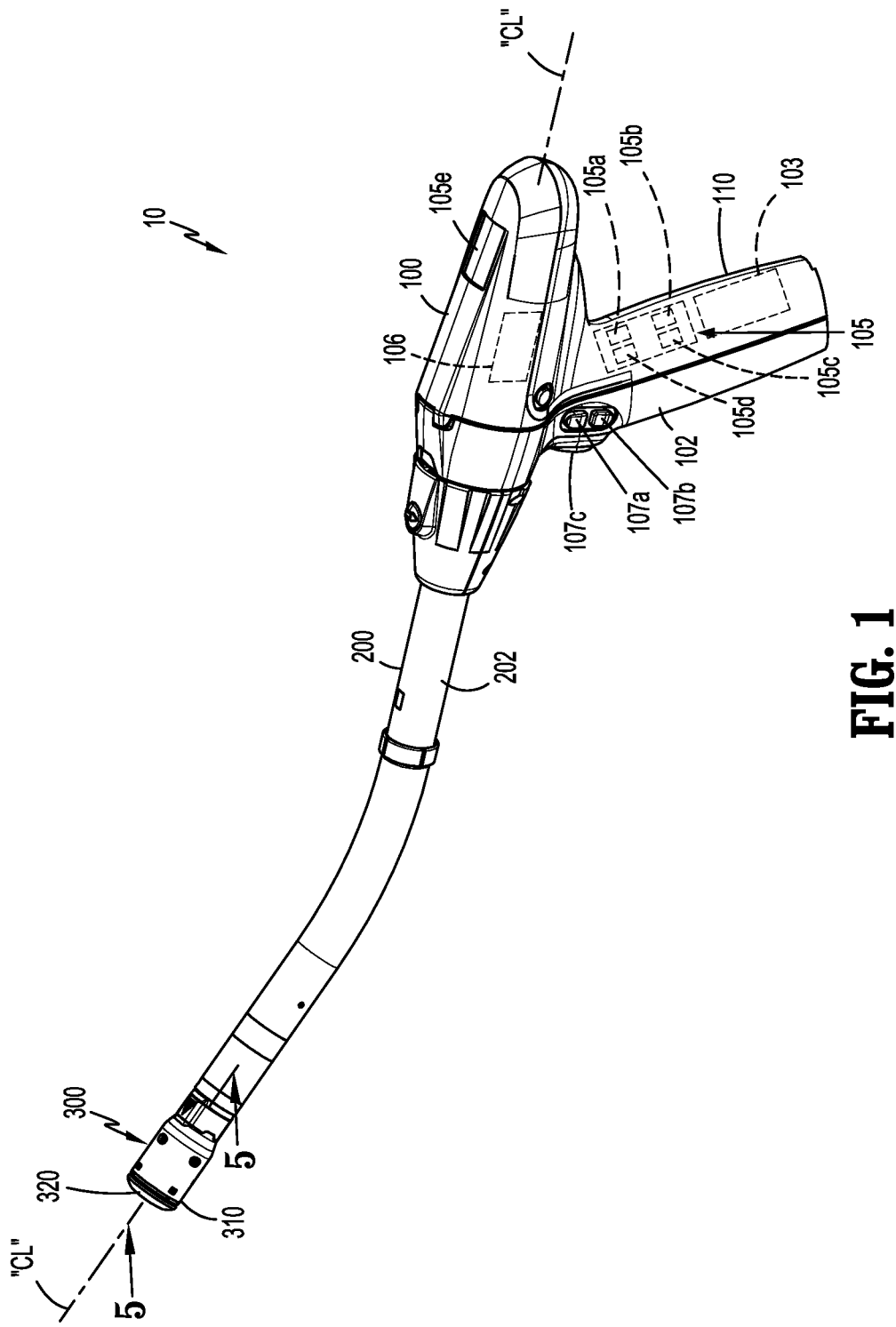
FIG. 1 is a perspective view of a surgical stapling apparatus in accordance with the principles of this disclosure.

Aspects of the disclosed surgical stapling apparatus are described in detail with reference to the drawings, in which like reference numerals designate identical or corresponding elements in each of the several views. As commonly known, the term "clinician" refers to a doctor, a nurse, or any other care provider and may include support personnel. Additionally, the term "proximal" refers to the portion of structure that is closer to the clinician and the term "distal" refers to the portion of structure that is farther from the clinician. In addition, directional terms such as front, rear, upper, lower, top, bottom, and the like are used simply for convenience of description and are not intended to limit the disclosure attached hereto.

In the following description, well-known functions or constructions are not described in detail to avoid obscuring the present disclosure in unnecessary detail.

Further, although the surgical instrument described herein is provided in connection with a powered surgical stapling apparatus for brevity, the disclosed surgical instrument can include any powered, manual, or robotically-controlled surgical instruments such as a clip applier, stitching device, energy-based device (e.g., a bipolar or monopolar forceps) or the like, and/or other surgical stapling apparatus such as a laparoscopic stapler, a transverse stapler, or an open stapler. For a detailed description of the structure and function of exemplary surgical stapling apparatus, one or more components of which may be included, or modified for use with the disclosed aspects, reference may be made to U.S. Pat. Nos. 8,256,656; 8,1571,152; 7,819,896; 7,334,717; 7,128,253; 5,964,394; and 5,915,616, the entire contents of each of which is incorporated herein by reference.

In general, a powered surgical stapling apparatus in accordance with this disclosure utilizes a powered handle with an adapter for effectuating end-to-end anastomosis ("EEA") procedures. The adapter supports an EEA reload having an end effector that supports staples and a knife to perform the EEA procedure. In accordance with principles of this disclosure, knife and staple component positions are monitored to ensure proper staple and cut stroke have been effectuated. In particular, this disclosure describes methods and structure for monitoring when the knife has reached sufficient stroke to perform a complete tissue cut. Positioning of the knife and tissue cut status has been determined by monitoring motor position of actuators and then calculating the actuator position using mechanics of the adapter; however, to limit any error resulting from compression of materials occurring within the adapter and/or overcompensation, this disclosure details methods and structure using electronics to determine when the knife has fully cut the tissue. More specifically, mechanical components of the surgical stapling apparatus are provided as part of an electronic circuit with electronic components such that when the knife pierces an anvil of the EEA reload, an amount of current or resistance can be measured indicative of a complete cut. In other words, current will flow more freely once the cut is complete as the high resistance of the tissue will be removed. Although aspects of this disclosure are described herein in connection with a 1-wire electronic assembly, in various aspects, any number of wires can be provided.

Figure 2:
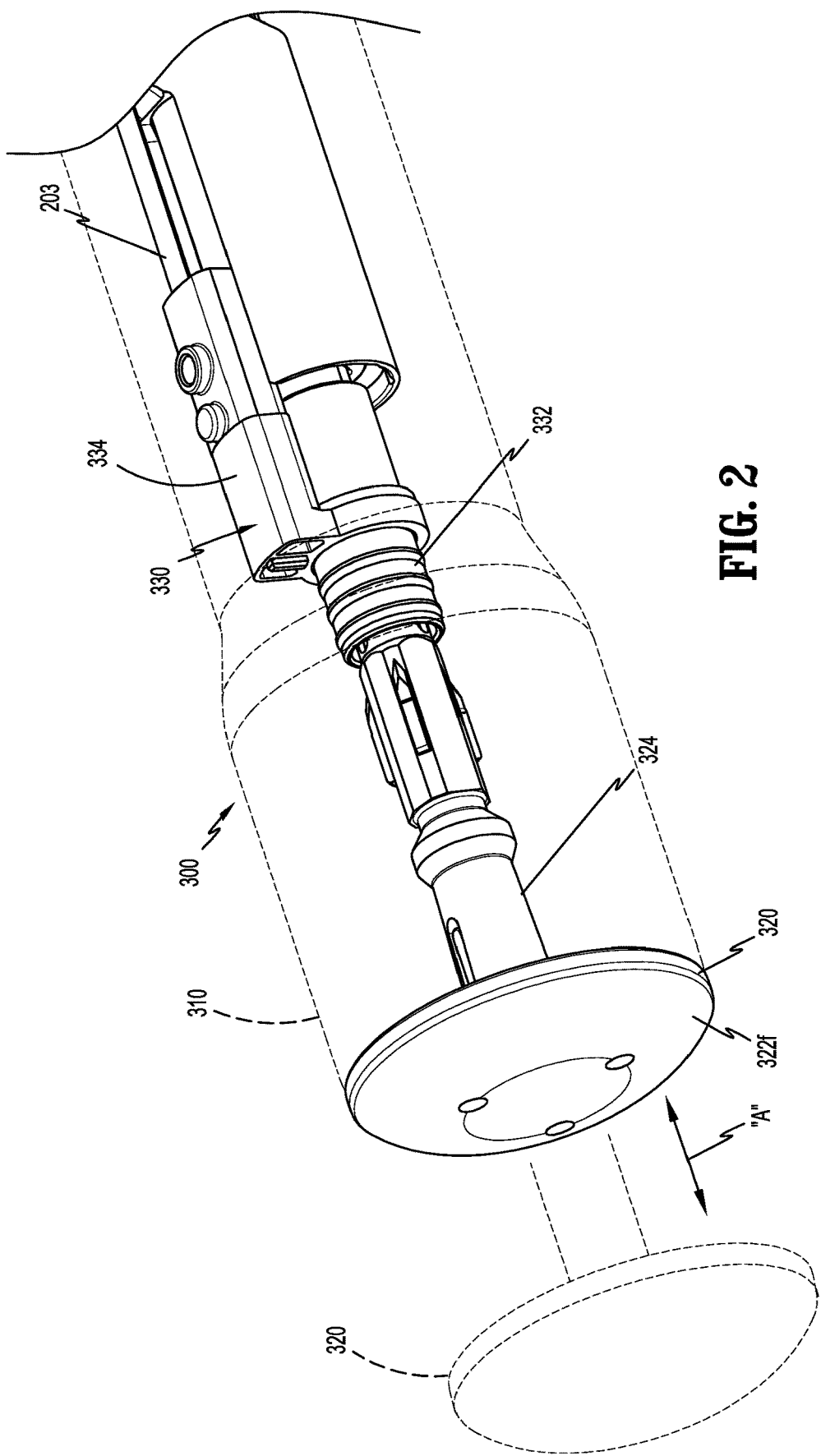
FIG. 2 is an enlarged, perspective view of a distal end portion of the surgical stapling apparatus of FIG. 1 with portions thereof removed for clarity.
Figure 3:
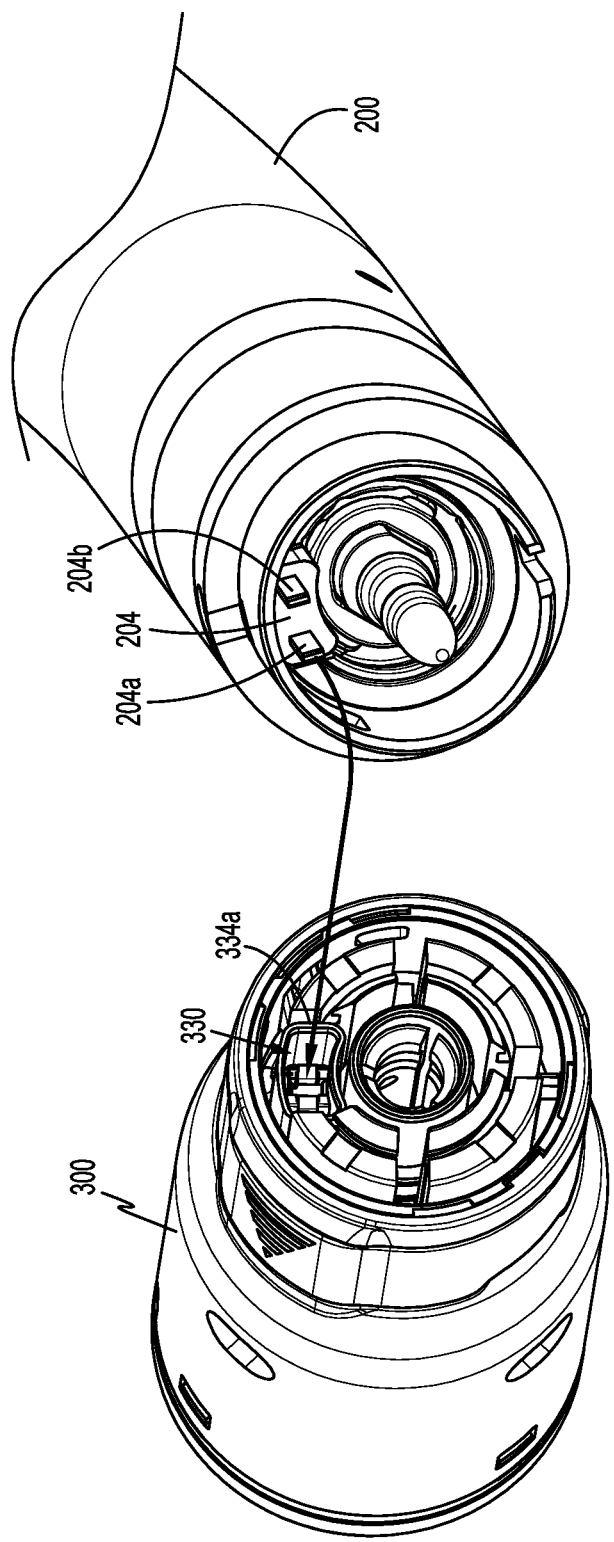
FIG. 3 is a perspective view, with parts separated, of the distal end portion of the surgical stapling apparatus of FIG. 2.

Turning now to FIGS. 1-3, a surgical stapling apparatus, generally referred to as 10, is illustrated. Surgical stapling apparatus 10 can be adapted for reuse and, in certain aspects, the surgical stapling apparatus 10, or portions thereof, may be adapted for a single use and/or may be disposable. Surgical stapling apparatus 10 defines a centerline "CL" and includes a surgical device 100 in the form of a powered handheld electromechanical instrument. Surgical stapling apparatus 10 further includes an adapter assembly 200 that is selectively attachable to surgical device 100. Adapter assembly 200 extends distally from surgical device 100 and has an elongated body 202 that extends to a distal end portion supporting an end effector 300 (e.g., a reload). End effector 300 includes a shell or cartridge assembly 310 and an anvil assembly 320 that are positionable between an unclamped or unapproximated position (see FIG. 2) and a clamped or approximated position (see FIG. 1) to selectively clamp tissue therebetween for selectively stapling and/or cutting the clamped tissue. Surgical device 100 is configured for selective connection with adapter assembly 200, and, in turn, adapter assembly 200 is configured for selective connection with end effector 300 (see FIG. 3). Together, surgical device 100 and adapter assembly 200 cooperate to operate end effector 300.

As can be appreciated, end effector 300, or portions thereof, may wholly or partially include electrically conductive material (e.g., metallic material) to facilitate electrical communication between components thereof.

Surgical device 100 of surgical stapling apparatus 10 includes a handle housing 102 configured for selective removable receipt of a rechargeable battery 103. Battery 103 is configured to supply power to electrical components of surgical device 100. Handle housing 102 supports a controller or circuit board 105 therein that is configured to control various operations of surgical device 100, and which includes any number of electronic components such as memory 105a, a processor 105b, a network interface 105c, and/or other input/output modules 105d. Controller 105 may be coupled to a display device 105e for outputting information and/or data such as a condition of components of surgical stapling apparatus 10 and/or tissue grasped be end effector 300.

Surgical stapling apparatus 10 further includes a drive mechanism 106 configured to drive rotatable shafts and/or gear components (not shown) within handle housing 102 in order to perform various operations of surgical stapling apparatus 10. For instance, drive mechanism 106 may be operable to selectively rotate end effector 300 about, and/or relative to, the centerline "CL" of surgical stapling apparatus 10; to selectively move anvil assembly 320 relative to the cartridge assembly 310 to selectively clamp tissue; and/or to fire surgical stapling apparatus 10 for fastening and/or cutting the clamped tissue. Battery 103, controller 105, and/or drive mechanism 106 may be operably coupled to one or more actuators 107a, 107b, and 107c such as finger-actuated control buttons, rocker devices, and/or the like to effectuate various functions of surgical stapling apparatus 10 such as those described above.

Drive mechanism 106 of electromechanical surgical stapling apparatus 10 includes an approximation mechanism 108 (see FIG. 5) that extends distally through elongated body 202 to an anvil retainer 108a that secures anvil assembly 320 to cartridge assembly 310. For instance, approximation mechanism 108 is configured to selectively or removably couple to anvil assembly 320 as described in U.S. Pat. No. 7,303,106 to Milliman et al., the entire contents of which are incorporated by reference herein. Approximation mechanism 108 is also configured to move along centerline "CL" of surgical stapling apparatus 10, between distal and proximal positions, to move anvil assembly 320 between approximated (e.g., closed) and unapproximated (e.g., open) positions relative to cartridge assembly 310, as indicated by arrows "A" (FIG. 2) to selectively clamp and/or unclamp tissue.

Reference may be made to U.S. Pat. No. 8,806,973 to Ross et al., the entire contents of which are incorporated herein by reference, for a detailed description of the construction and operation of an example electromechanical surgical stapling apparatus, the components of which are combinable and/or interchangeable with one or more components of surgical stapling apparatus 10 described herein.

Although surgical stapling apparatus 10 is described as an electromechanically powered surgical stapling apparatus, the presently disclosed surgical stapling apparatus can be provided as a manually powered stapling apparatus. For a more detailed description of the construction and operation of an exemplary manually powered stapling apparatus, one or more components of which can be combined and/or interchanged with the electromechanically powered stapling apparatus described herein, reference can be made to U.S. Pat. No. 5,915,616 to Viola et al., U.S. Pat. No. 8,109,426 to Milliman et al., U.S. Pat. No. 8,272,552 to Holsten et al., U.S. Pat. No. 9,504,470 to Milliman, and U.S. Pat. No. 9,414,839 to Penna, the entire contents of each of which are incorporated by reference herein.

Figure 4:
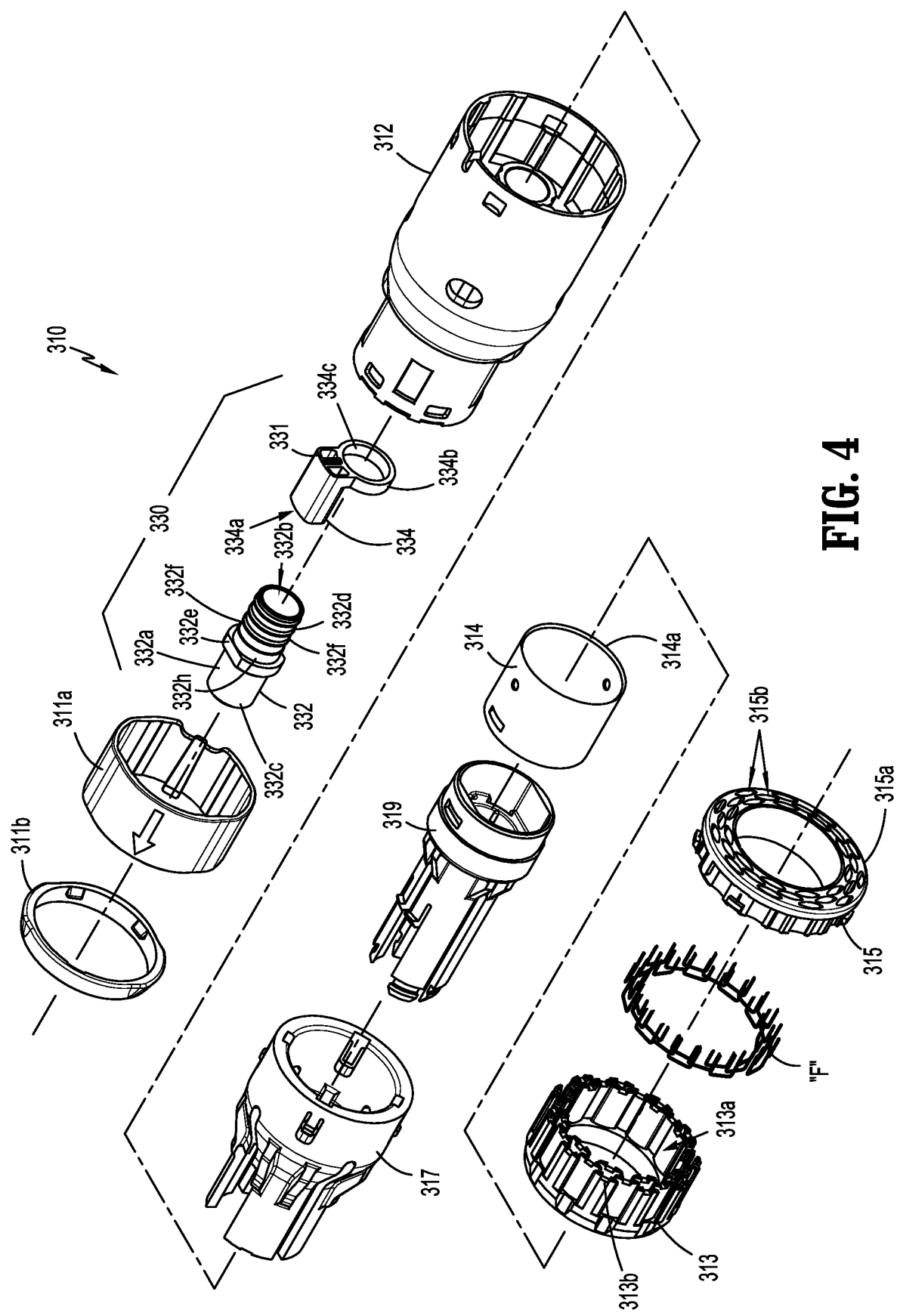
FIG. 4 is a perspective view, with parts separated, of an end effector of the surgical stapling apparatus of FIG. 1.
Figure 5:
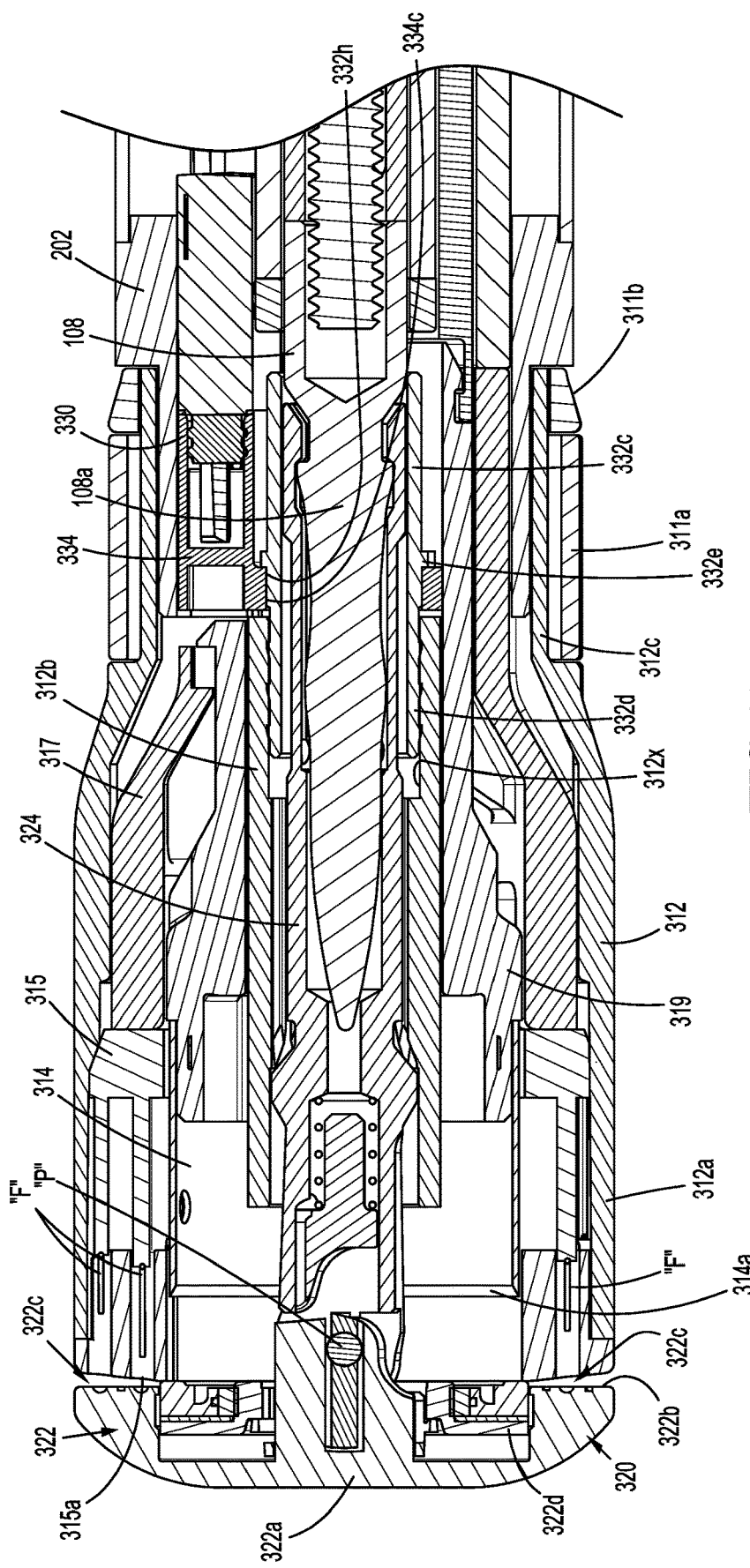
FIG. 5 is an enlarged, cross-sectional view of the distal end portion of the surgical stapling apparatus of FIG. 1 as taken along section line 5-5 of FIG. 1 when the end effector thereof is in a first position.
Figure 6:
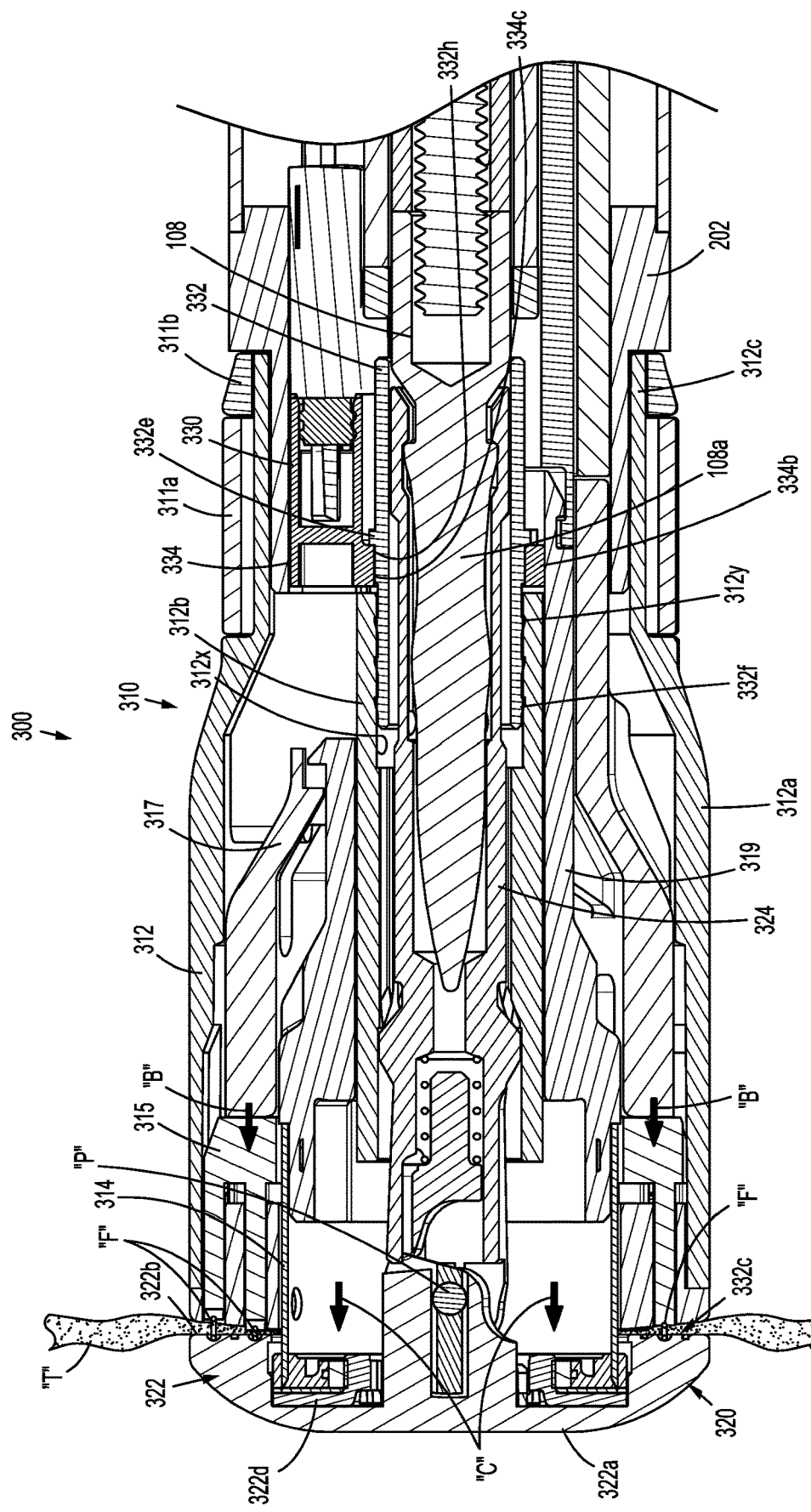
FIG. 6 is another cross-sectional view taken along section line 5-5 of FIG. 1 when the end effector is in a second position.

Turning now to FIGS. 4, 5, and 6, anvil assembly 320 of end effector 300 includes an anvil head assembly 322 and a center rod assembly 324 that extends proximally from anvil head assembly 322. Anvil head assembly 322 is pivotally coupled to center rod assembly 324 about a pivot "P" to enable anvil head assembly 322 to move from an untilted position to a tilted position (not shown) after end effector 300 is fired and anvil assembly is unapproximated from cartridge assembly 310. Briefly, anvil head assembly 322 includes an anvil head 322a having a bottom surface 322b that defines one or more arrays of staple forming pockets 322c therein for forming fasteners "F" supported in cartridge assembly 310. Anvil head 322a also includes a backup plate assembly 322d movably supported in anvil head 322a. As seen in FIG. 2, anvil head assembly 322 may include an anvil cap 322f that may include insulated material. For a more detailed description of anvil assembly 320 and/or operation thereof, reference can be made to U.S. Pat. Nos. 7,303,106 and 8,109,426 to Milliman et al., each of which is incorporated by reference herein above.

Cartridge assembly 310 of end effector 300 includes a shell 312, a pusher 313 for firing fasteners "F" into anvil assembly 320, a cylindrical knife 314 for cutting tissue, a staple cartridge 315 for supporting fasteners "F" in cartridge assembly 310. Cartridge assembly 310 further includes an outer drive sleeve 317 configured to distally advance pusher 313 relative to staple cartridge 315, as indicated by arrows "B," and an inner drive sleeve 319 supported on outer drive sleeve 317. Inner drive sleeve 319 is configured to distally advance cylindrical knife 314 relative to staple cartridge 315, as indicated by arrows "C," when outer drive sleeve 317 distally advances pusher 313 relative to staple cartridge 315 for forming fasteners "F" (e.g., staples) against anvil head 322a of anvil assembly 320.

Shell 312 of cartridge assembly 310 is secured to a distal end portion of elongated body 202 of adapter assembly 202 (FIG. 1) via an outer collar 311a and ring 311b. Shell 312 includes an outer housing 312a configured to support staple cartridge 315, and an inner housing 312b configured to receive center rod assembly 324 of anvil assembly 320 therein, and a coupling portion 312c configured to couple cartridge assembly 310 to elongated body 202 of adapter assembly 200.

Pusher 313 of cartridge assembly 310 is slidably positioned about inner housing 312b of shell 312 and defines a central throughbore 313a. Pusher 313 includes annular arrays of distally extending fingers 313b configured to support an array of fasteners "F." One or more of fingers 313b and/or one or more of fasteners "F" may have different heights. In some aspects, one or more of fingers 313b and/or one or more of fasteners "F" may have the same height.

Cylindrical knife 314 of cartridge assembly 310 is frictionally retained within central throughbore 313a of pusher 313 to fixedly secure knife 314 in relation to pusher 313. The distal end of knife 314 includes a circular cutting edge 314a configured to severe tissue.

Staple cartridge 315 of cartridge assembly 310 includes a tissue contact surface 315a in which annular arrays of slots 315b are formed. Annular arrays of slots 315b of the staple cartridge 315 are configured to support and slidably receive annular arrays of fasteners "F" therein.

End effector 300 further includes an electronics assembly 330, which may be in the form of a device communication bus system that is configured to electrically couple to a plug 204 (FIG. 3) supported in elongated body portion 202 that is electrically coupled to one or more components of surgical instrument 100, such as battery 103 and/or controller 105 thereof, via an electrical ribbon 203 extending proximally from plug 204. Electrical ribbon 203 includes any number of cables, wires, etc., to electrically communicate data, power, signals from/to controller 105 and/or battery 103. In aspects, a battery may be provided in the electronics assembly, in the alternative and/or in addition to battery 103 supported by surgical device 100. Such additional and/or alternative battery may function to provide power to electronics assembly and/or other components of surgical stapling apparatus 10. Electronics assembly 330 is configured to provide data signaling, and/or power over one or more conductors. For example, electronic assembly 330 supports one or more electronic components 331 that can include a device communication bus system such as 1-Wire technology including a capacitor (e.g., 800 pF) to store charge and to provide power with only two wires, a data wire and a ground wire. The data wire can be a single open drain wire including a single pull-up resistor. As can be appreciated, electronic components 331 can include any other suitable serial communication systems such as CAN bus, SD-12, I$^2$C, Micro-Lan, USB, SATA or the like. Moreover, such serial communication systems can be provided in any number of type of packages such as an integrated circuit, TO-92, or the like. Electronic assembly 330 is configured to measure a resistance between electrical paths in electrical communication therewith. An amount of resistance between electrical paths can be indicative of, for example, tissue cut, tissue cutting, or tissue uncut, depending on an amount of resistance so that electronic assembly 330 and/or a controller (e.g., controller 105 or other networked controller—not shown—in operative communication with electronic assembly 330) can determine when a tissue cut (e.g., complete and/or partial) has occurred. In aspects, electronics assembly 330 may support one or more controllers to facilitate operation of electronics assembly 330 and/or one or more other components of surgical stapling apparatus 10.

Electronics assembly 330 of end effector 300 can be disposed within cartridge assembly 310 and includes an inner coupler 332 and an outer coupler 334. Inner coupler 332 has a tubular body 332a defining a passage 332b therethrough and having a proximal portion 332c and a distal portion 332d separated by a retention nut 332e. Distal portion 332d includes a plurality of longitudinally spaced-apart ribs 332f on an outer surface thereof that engage an inner surface 312x of inner housing 312b of shell 312 to secure inner coupler 332 to inner housing 312b. The outer surface of distal portion 332d of inner coupler 332 further includes an annular outer conductive surface 332h on a proximal end portion thereof that is adjacent to retention nut 332e. Annular conductive surface 332h may be raised relative to ribs 332f but recessed relative to retention nut 332e. Inner surface 312x can include recesses 312y defined therein for receiving ribs 332f of inner coupler 332. Inner coupler 332 of electronics assembly 330 includes an inner surface 332g that defines passage 332b for receiving center rod assembly 324 of anvil assembly 320 and anvil retainer 108a of approximation assembly 108 therein. The outer surface of center rod assembly 324 of anvil assembly 320 and is disposed in contact with inner surface 332g of inner coupler 332 to facilitate support of center rod assembly 324 and anvil retainer 324, and enable electrical communication between inner coupler 332 and center rod assembly 324. Both center rod assembly 324 and inner coupler 332 include conductive material (e.g., metallic material) at least along contact locations between center rod assembly 324 and inner coupler 332. Outer coupler 334 includes a socket 334a for receiving pins 204a, 204b of plug 204 and a coupling ring 334b depending therefrom. Coupling ring 334b of outer coupler 334 is positioned to receive inner coupler 332 therein such that coupling ring 334b of outer coupler 334 abuts retaining nut 332e of inner coupler 332 and is mounted onto annular outer conductive surface 332h of inner coupler 332. Coupling ring 334b includes an annular inner conductive surface 334c that contacts outer annular conductive surface 332h of inner coupler 332 to electrically communicate therewith.

Referring now to FIGS. 1-6, in operation, once end effector 300 of the surgical stapling apparatus 10 is positioned adjacent to a surgical site, anvil assembly 320 of end effector 300 can be approximated toward cartridge assembly 310 of end effector 300 to grasp tissue between cartridge and anvil assemblies 310, 320 and to create an electrical circuit from electronics assembly 330 in cartridge assembly 310 through the grasped tissue "T" and anvil assembly 320 and back to electronics assembly 330. Before tissue "T" is grasped, no current flows from cartridge assembly 310 to anvil assembly 320.

Once the tissue "T" is grasped and the electrical circuit is created through the tissue "T", an amount of current in the electrical circuit can be measured. Current will be low due to the high resistance of the tissue "T" and will gradually increase until the tissue "T" is severed and knife 314 of cartridge assembly 310 contacts backplate 322d of anvil assembly 320 so that resistance from the "T" is eliminated and currently can freely flow between the cartridge and anvil assemblies 310, 320.

With reference to FIG. 6, when stapling apparatus 10 is fired, outer and inner drive sleeves 317, 319 distally advance pusher 313 and cylindrical knife 314 for firing fasteners "F" into tissue "T" and cutting the tissue "T."

As discussed above, electronics assembly 330 is electrically coupled to controller 105 and battery 103 via electrical ribbon 203 so that data or information can be analyzed (e.g., in real-time) to determine characteristics, properties, and/or conditions of the tissue and/or positions of one or more components of surgical stapling apparatus 10. Such data and/or information can include an amount of current flowing through the electrical circuit and/or a resistance of the tissue. Additionally, and or alternatively, positioning of one or more of the various components of surgical stapling apparatus 10 can be determined. In one example, based on an amount of current or resistance measured by electronics assembly 330 and/or controller 105," electronics assembly 330 and/or controller 105 can determine whether, or to what degree, tissue (or an amount thereof) has been cut or not and/or whether the components of surgical stapling apparatus 10, such the knife 314 and/or inner sleeve 319, have been displaced a predetermined distance corresponding to an amount of current or resistance in the electronic circuit defined through the tissue. A higher resistance value or lower current value may indicate tissue or portions thereof have not been cut and a lower resistance value or higher current value may indicate that tissue has been wholly or partially cut.

Indeed, once cylindrical knife 314 cuts through the tissue "T" and engages (e.g., pierces) anvil assembly 320, more specifically, for instance, backup plate assembly 322d thereof, electrical energy can be freely conducted through anvil and cartridge assemblies 310, 320, electronics assembly 330, plug 204, cable ribbon 203, controller 105, battery 103, e (or other energy source such a generator or electrical outlet to which surgical stapling device may couple), etc. Notably, in aspects, electronics assembly 330 may be electrically coupled to one or more controllers and/or batteries supported therein for effectuating any number of operations of surgical stapling apparatus 10 such as measuring, analyzing, and/or outputting data from the electrical circuit. Such controllers and/or batteries may be in place of, or in addition to controller 105 and battery 103. Electronics assembly 330 and/or any controllers coupled thereto (e.g., controller 105) may provide an output such as an indication or alarm which may be audible, tactile, and/or visible that may be indicative of a status or condition of the electrical circuit, tissue cut state, positioning of one or more components of surgical stapling apparatus 10, etc. For instance, such output can be provided through a display 105e, which may be local to surgical stapling apparatus 10 or remote therefrom (e.g., on a remote computing device).

Once tissue cut is complete, anvil assembly 320 of end effector 300 can be unapproximated or separated from cartridge assembly 310 of end effector 300 (and tilted as discussed above) to release the stapled tissue and remove end effector 300 from the surgical site. Anvil and/or cartridge assemblies 310, 320 can be removed from the surgical stapling apparatus 10 and/or replaced. For a more detailed description of firing, cutting, and/or fastening of fasteners "F" and/or replacement of anvil and/or cartridge assemblies 310, 320, reference can be made to U.S. Pat. No. 7,303,106, incorporated herein by reference above.

Further, the various aspects disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Moreover, the disclosed electronic structure such as the electronic assembly and/or controllers, can include any suitable electrical components for operating the disclosed surgical stapling apparatus or components thereof. Such electrical components can include, for example, one or more controllers and/or circuitry, which may include or be coupled to one or more printed circuit boards. As used herein, the term "controller" includes "processor," "digital processing device" and like terms, and are used to indicate a microprocessor or central processing unit (CPU). The CPU is the electronic circuitry within a computer that carries out the instructions of a computer program by performing the basic arithmetic, logical, control and input/output (I/O) operations specified by the instructions, and by way of non-limiting examples, include server computers. In some aspects, the controller includes an operating system configured to perform executable instructions. The operating system is, for example, software, including programs and data, which manages hardware of the disclosed surgical stapling apparatus and provides services for execution of applications for use with the disclosed surgical stapling apparatus. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. In some aspects, the operating system is provided by cloud computing.

In some aspects, the term "controller" may be used to indicate a device that controls the transfer of data from a computer or computing device to a peripheral or separate device and vice versa, and/or a mechanical and/or electro-mechanical device (e.g., a lever, knob, etc.) that mechanically operates and/or actuates a peripheral or separate device.

In aspects, the controller includes a storage and/or memory device. The storage and/or memory device is one or more physical apparatus used to store data or programs on a temporary or permanent basis. In some aspects, the controller includes volatile memory and requires power to maintain stored information. In various aspects, the controller includes non-volatile memory and retains stored information when it is not powered. In some aspects, the non-volatile memory includes flash memory. In certain aspects, the non-volatile memory includes dynamic random-access memory (DRAM). In some aspects, the non-volatile memory includes ferroelectric random access memory (FRAM). In various aspects, the non-volatile memory includes phase-change random access memory (PRAM). In certain aspects, the controller is a storage device including, by way of non-limiting examples, CD-ROMs, DVDs, flash memory devices, magnetic disk drives, magnetic tapes drives, optical disk drives, and cloud computing based storage. In various aspects, the storage and/or memory device is a combination of devices such as those disclosed herein.

In some aspects, the controller includes a display to send visual information to a user. In various aspects, the display is a cathode ray tube (CRT). In various aspects, the display is a liquid crystal display (LCD). In certain aspects, the display is a thin film transistor liquid crystal display (TFT-LCD). In aspects, the display is an organic light emitting diode (OLED) display. In certain aspects, on OLED display is a passive-matrix OLED (PMOLED) or active-matrix OLED (AMOLED) display. In aspects, the display is a plasma display. In certain aspects, the display is a video projector. In various aspects, the display is interactive (e.g., having a touch screen or a sensor such as a camera, a 3D sensor, a LiDAR, a radar, etc.) that can detect user interactions/gestures/responses and the like. In some aspects, the display is a combination of devices such as those disclosed herein.

The controller may include or be coupled to a server and/or a network. As used herein, the term "server" includes "computer server," "central server," "main server," and like terms to indicate a computer or device on a network that manages the surgical stapling apparatus, components thereof, and/or resources thereof. As used herein, the term "network" can include any network technology including, for instance, a cellular data network, a wired network, a fiber optic network, a satellite network, and/or an IEEE 802.11a/b/g/n/ac wireless network, among others.

In various aspects, the controller can be coupled to a mesh network. As used herein, a "mesh network" is a network topology in which each node relays data for the network. All mesh nodes cooperate in the distribution of data in the network. It can be applied to both wired and wireless networks. Wireless mesh networks can be considered a type of "Wireless ad hoc" network. Thus, wireless mesh networks are closely related to Mobile ad hoc networks (MANETs). Although MANETs are not restricted to a specific mesh network topology, Wireless ad hoc networks or MANETs can take any form of network topology. Mesh networks can relay messages using either a flooding technique or a routing technique. With routing, the message is propagated along a path by hopping from node to node until it reaches its destination. To ensure that all its paths are available, the network must allow for continuous connections and must reconfigure itself around broken paths, using self-healing algorithms such as Shortest Path Bridging. Self-healing allows a routing-based network to operate when a node breaks down or when a connection becomes unreliable. As a result, the network is typically quite reliable, as there is often more than one path between a source and a destination in the network. This concept can also apply to wired networks and to software interaction. A mesh network whose nodes are all connected to each other is a fully connected network.

In some aspects, the controller may include one or more modules. As used herein, the term "module" and like terms are used to indicate a self-contained hardware component of the central server, which in turn includes software modules. In software, a module is a part of a program. Programs are composed of one or more independently developed modules that are not combined until the program is linked. A single module can contain one or several routines, or sections of programs that perform a particular task.

As used herein, the controller includes software modules for managing various aspects and functions of the disclosed surgical stapling apparatus or components thereof.

The disclosed surgical stapling apparatus may also utilize one or more controllers to receive various information and transform the received information to generate an output. The controller may include any type of computing device, computational circuit, or any type of processor or processing circuit capable of executing a series of instructions that are stored in memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, cause the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

As can be appreciated, securement of any of the components of the disclosed apparatus can be effectuated using known securement techniques such welding, crimping, gluing, fastening, etc.

Persons skilled in the art will understand that the structures and methods specifically described herein and illustrated in the accompanying figures are non-limiting exemplary aspects, and that the description, disclosure, and figures should be construed merely as exemplary of particular aspects. It is to be understood, therefore, that this disclosure is not limited to the precise aspects described, and that various other changes and modifications may be effectuated by one skilled in the art without departing from the scope or spirit of the disclosure. Additionally, it is envisioned that the elements and features illustrated or described in connection with one exemplary aspect may be combined with the elements and features of another without departing from the scope of this disclosure, and that such modifications and variations are also intended to be included within the scope of this disclosure. Indeed, any combination of any of the disclosed elements and features is within the scope of this disclosure. Accordingly, the subject matter of this disclosure is not to be limited by what has been particularly shown and described.

What is claimed is:

1. A surgical stapling apparatus, comprising:
    an end effector having an anvil assembly and a cartridge assembly, the anvil and cartridge assemblies positionable between an open position and a closed position to selectively grasp tissue therebetween; and
    an electronics assembly supported in the cartridge assembly and configured to determine a condition of the grasped tissue based on an amount of current in an electrical circuit defined by the anvil and cartridge assemblies, wherein the electronics assembly includes an inner coupler and an outer coupler, the inner and outer couplers supported in the cartridge assembly independent of the anvil assembly and configured to receive the anvil assembly when electrically coupled together in the cartridge assembly.

2. The surgical stapling apparatus of claim 1, further comprising a knife supported in the cartridge assembly and positioned to contact the anvil assembly to change the amount of current in the electrical circuit.

3. The surgical stapling apparatus of claim 2, wherein the electronics assembly is configured to determine when the grasped tissue is cut by the knife based on the amount of current.

4. The surgical stapling apparatus of claim 1, wherein current is prevented from flowing through the electrical circuit before the tissue is grasped.

5. The surgical stapling apparatus of claim 1, wherein the outer coupler supports the inner coupler therein.

6. The surgical stapling apparatus of claim 5, wherein the inner coupler has a tubular body positioned to receive a center rod assembly of the anvil assembly therein.

7. The surgical stapling apparatus of claim 5, wherein the outer coupler includes a coupling ring that depends therefrom and is positioned to receive the inner coupler therein.

8. The surgical stapling apparatus of claim 7, wherein the coupling ring is disposed in contact with a drive sleeve supported within the end effector.

9. The surgical stapling apparatus of claim 8, wherein the drive sleeve is movable relative to the anvil assembly to enable a knife to cut through tissue grasped between the anvil assembly and the cartridge assembly.

10. The surgical stapling apparatus of claim 1, wherein the electronics assembly includes a device communication bus system with a single data wire.

11. A surgical stapling apparatus, comprising:
    a powered surgical device; and
    an adapter assembly extending distally from the powered surgical device and supporting an end effector, the end effector including:
        an anvil assembly and a cartridge assembly, the anvil and cartridge assemblies positionable between an open position and a closed position to selectively grasp tissue therebetween;

an inner coupler and an outer coupler, the inner and outer couplers supported in the cartridge assembly independent of the anvil assembly, the inner and outer couplers electrically coupled together and positioned in the cartridge assembly to receive the anvil assembly therein; and a controller configured to determine a condition of the grasped tissue based on a condition of an electrical circuit defined by components of the end effector.

12. The surgical stapling apparatus of claim 11, wherein a first component of the components of the end effector is positioned to contact the anvil assembly to change the condition of the electrical circuit.

13. The surgical stapling apparatus of claim 12, wherein when the first component contacts the anvil assembly, the controller is configured to output an indication that the grasped tissue is cut.

14. The surgical stapling apparatus of claim 12, wherein the first component includes a knife, and wherein a drive sleeve is movable relative to the anvil assembly to enable the knife to cut through tissue grasped between the anvil assembly and the cartridge assembly.

15. The surgical stapling apparatus of claim 11, wherein the condition of the electrical circuit includes an amount of current in the electrical circuit.

16. The surgical stapling apparatus of claim 11, wherein at least one of the inner coupler or the outer coupler supports a device communication bus system.

17. The surgical stapling apparatus of claim 16, wherein the inner coupler has a tubular body positioned to receive a center rod assembly of the anvil assembly therein.

18. The surgical stapling apparatus of claim 16, wherein the outer coupler includes a coupling ring that depends therefrom and is positioned to receive the inner coupler therein.

19. The surgical stapling apparatus of claim 18, wherein the coupling ring is disposed in contact with a drive sleeve supported within the end effector.

20. A surgical stapling apparatus, comprising:

a powered surgical device;

an adapter assembly extending distally from the powered surgical device and supporting an end effector configured to grasp tissue, the end effector including an anvil assembly and a cartridge assembly, the cartridge assembly including an inner coupler and an outer coupler that are electrically coupled together in the cartridge assembly independent of the anvil assembly, the inner and outer couplers positioned in the cartridge assembly to receive the anvil assembly therein;

a device communication bus system supported in the end effector and in contact with components of the end effector to define an electrical circuit; and a controller including a processor and a memory having instructions stored thereon, which when executed by the processor, cause the device communication bus system to measure a current in the electrical circuit to enable the processor to determine a condition of the grasped tissue.

* * * * *